United States Patent

Sacherer

(10) Patent No.: US 8,758,382 B2
(45) Date of Patent: Jun. 24, 2014

(54) LANCET MAGAZINE

(75) Inventor: Klaus-Dieter Sacherer, Kirchheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 349 days.

(21) Appl. No.: 12/731,865

(22) Filed: Mar. 25, 2010

(65) Prior Publication Data

US 2010/0234869 A1    Sep. 16, 2010

Related U.S. Application Data

(63) Continuation of application No. PCT/EP2008/007117, filed on Aug. 30, 2008.

(30) Foreign Application Priority Data

Sep. 26, 2007 (EP) .................................. 07018880

(51) Int. Cl.
*A61B 17/32* (2006.01)

(52) U.S. Cl.
USPC ........................................................ 606/182

(58) Field of Classification Search
USPC .......... 606/181–183, 185–189; 600/573, 583; 604/22, 136–138
See application file for complete search history.

(56) References Cited

U.S. PATENT DOCUMENTS

| 5,133,730 A | 7/1992 | Biro et al. | |
|---|---|---|---|
| 5,395,388 A | 3/1995 | Schraga | |
| 6,929,649 B2 | 8/2005 | Pugh | |
| 2003/0028126 A1* | 2/2003 | List | 600/583 |
| 2004/0049220 A1* | 3/2004 | Boecker et al. | 606/181 |
| 2005/0015020 A1* | 1/2005 | LeVaughn et al. | 600/583 |
| 2006/0100543 A1* | 5/2006 | Raney et al. | 600/583 |
| 2006/0155317 A1 | 7/2006 | List | |
| 2006/0224172 A1* | 10/2006 | LeVaughn et al. | 606/181 |
| 2006/0264996 A1* | 11/2006 | LeVaughn et al. | 606/181 |
| 2007/0179404 A1 | 8/2007 | Escutia et al. | |
| 2007/0292314 A1 | 12/2007 | Effenhauser et al. | |
| 2008/0064987 A1 | 3/2008 | Escutia et al. | |

FOREIGN PATENT DOCUMENTS

| DE | 10 2004 059 491 | 7/2006 |
|---|---|---|
| EP | 1 658 897 | 5/2006 |
| WO | WO 9513750 | 5/1995 |
| WO | WO 2005018709 A2 * | 3/2005 |
| WO | WO 2007041244 | 4/2007 |

OTHER PUBLICATIONS

International Preliminary Report on Patentability; PCT/EP2008/007117; Aug. 30, 2008.

* cited by examiner

*Primary Examiner* — David Eastwood
(74) *Attorney, Agent, or Firm* — Bose McKinney & Evans LLP (57) ABSTRACT

The invention relates to a lancet magazine with a plurality of lancets for generating a puncture wound for collecting a sample of body fluid. According to the invention, the lancets in the lancet magazine are each coupled to a drive mechanism which, for each lancet, comprises at least one pretensioned drive element which, when the drive mechanism is triggered, releases mechanical energy to accelerate the lancet coupled thereto for a puncturing movement.

13 Claims, 6 Drawing Sheets

LANCET MAGAZINE

RELATED APPLICATIONS

This is a continuation application of International Patent Application Serial Number PCT/EP2008/007117, filed Aug. 30, 2008, which claims priority to EP 07018880.0, filed Sep. 26, 2007, both of which are hereby incorporated by reference in their entirety.

BACKGROUND

The present invention relates to a lancet magazine with a plurality of lancets for generating a puncture wound for collection of a sample of a body fluid. Lancet magazines of this kind are used with matching puncturing devices that successively use the lancets contained in the lancet magazine for generating a puncture wound.

Lancet magazines and matching puncturing devices are used, for example, by diabetics who must measure their blood-sugar level several times a day and need for that purpose a sample of a body liquid, as a rule, a sample of blood or interstitial liquid, which is obtained from a puncture wound produced by a puncturing system.

A puncturing system that comprises a puncturing device and matching lancet magazines has been known, for example, from DE 102004059491. That puncturing system uses a rotary magazine that contains six lancets. The puncturing device comprises a lancet drive with a drive rotor which is driven by a drive spring and which, for performing a puncturing action, advances and then retracts a tappet, coupled with the rotor, in the puncturing direction. In the course of that movement, the tappet is introduced through a push-in opening into the lancet magazine where it couples to a lancet, thereby pushing it out of an oppositely arranged exit opening of the lancet magazine so that a puncture wound can be produced in a part of a body applied to the puncturing opening of the device. Form-locking engagement between the tappet and the lancet ensures that the lancet is retracted into the lancet magazine by a retracting movement that follows the advancing movement. While the known puncturing system offers the user a high degree of comfort, the production costs are considerable for both the device and the matching lancet magazines.

SUMMARY

The present invention provides a puncturing system at reduced expense. According to certain exemplary embodiments, the lancets are each coupled to a drive mechanism which, for each lancet, comprises at least one pretensioned drive mechanism which, when the drive mechanism is triggered, releases mechanical energy to accelerate the respective coupled lancet for a puncturing movement. Although contrary to conventional puncturing systems where a single drive mechanism is provided to which the lancets of the magazine are coupled one by one, in the exemplary embodiments in which a separate drive mechanism is provided for each lancet, cost savings surprisingly can be realized. Assigning each lancet a drive mechanism with a pretensioned drive element allows the coupling mechanism between the drive and a lancet, and the drive as such, to be substantially simplified.

In addition, certain embodiments provide the advantage that any multiple use of a lancet that would give cause for concern for hygienic reasons can be reliably excluded because the drive element of a lancet will be relaxed after it has performed one puncturing action so that the lancet cannot be used again. A further advantage is that the puncturing system in exemplary embodiments can be made very small and compact and can still accommodate a relatively large supply of lancets. This is a considerable advantage for diabetics who have to check their blood-sugar level several times a day and who therefore always have to carry a puncturing device.

The lancets are typically provided in annular arrangement in the lancet magazine. This permits a greater number of lancets, for example, 20 to 50 lancets, to be arranged in an especially compact manner. However, a lancet magazine according to another embodiment may also be configured as a stack magazine.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Corresponding reference characters indicate corresponding parts throughout the several views.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
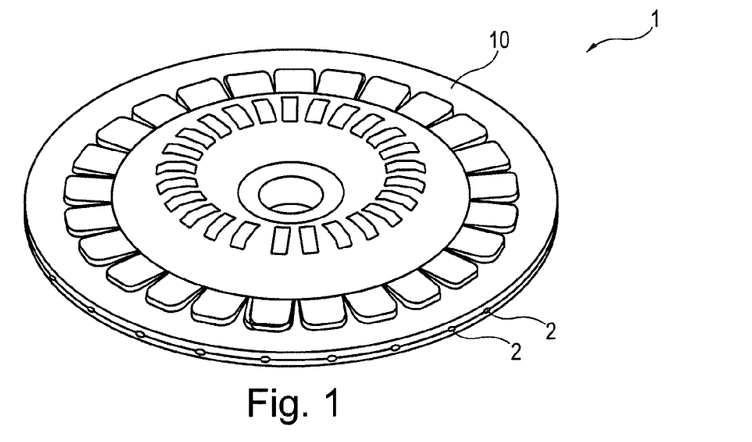
FIG. 1 is a perspective view of one embodiment of a lancet magazine.

FIG. 1 shows an embodiment of a lancet magazine 1. Such a lancet magazine is intended to be loaded into a puncturing device by which the lancets contained in the lancet magazine 1 are used one by one for generating a puncture wound. The disk-shaped lancet magazine 1 is provided, in its circumferential surface, with exit openings 2 through which the lancets contained in the lancet magazine 1 exit during use.

Figure 2:
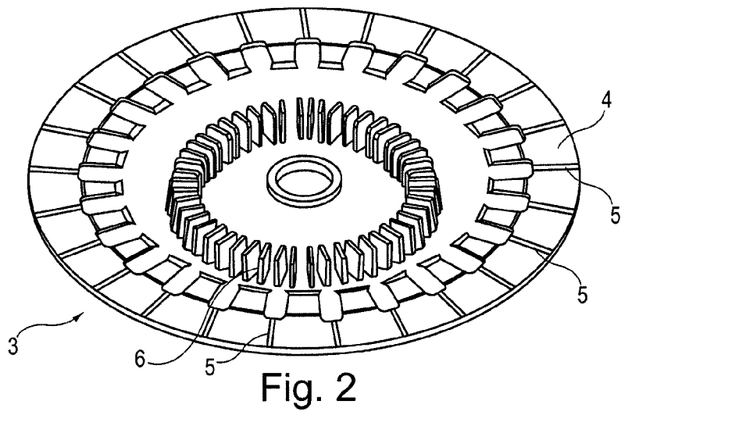
FIG. 2 is a perspective view of one half of the magazine housing of the embodiment illustrated in FIG. 1, shown in an open condition.

FIG. 2 shows one half 3 of the housing of the lancet magazine 1. The housing of the lancet magazine 1 includes two housing halves which can have an identical configuration to simplify production. However, the housing halves may also be given a different configuration. As can be seen in FIG. 1, the halves are in the form of disks.

In the assembled condition of the housing, the housing halves 3 are in contact one with the other via circumferential surfaces 4 provided with guide channels 5 for the lancets. The housing halves 3, which can be produced as injection-molded plastic parts, may be connected in a form-locking manner, for example, by bonding or welding. Preferably, however, the housing halves 3 are joined mechanically by connection elements 6.

In the illustrated embodiment, the connection elements 6 are configured as a ring of clamping ribs. As the two housing halves 3 are joined, the clamping ribs 6 of the two housing halves 3 come to engage each other so that the two housing halves 3 are held together by a clamping effect, i.e., by friction forces. However, there is also the possibility to design the connection elements 6 for form-locking connection of the housing halves 3.

Figure 3:
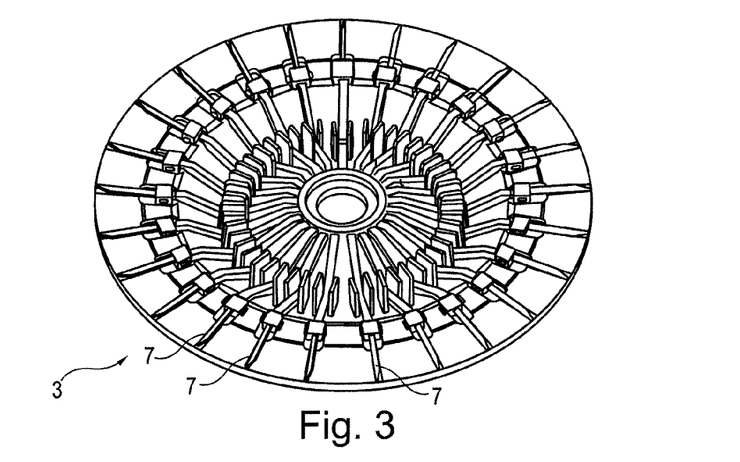
FIG. 3 is a perspective view of the half of the housing illustrated in FIG. 2, including loaded lancets.

FIG. 3 shows one housing half 3 according to FIG. 2 with loaded lancets 7. The lancets 7 lie in the guide channels 5 of the housing half 3 and extend in radial direction. Further details can be seen in FIG. 4 which shows a representation of a detail of FIG. 3. For the sake of simplicity, only a single lancet 7 has been illustrated in FIG. 4.

Figure 4:
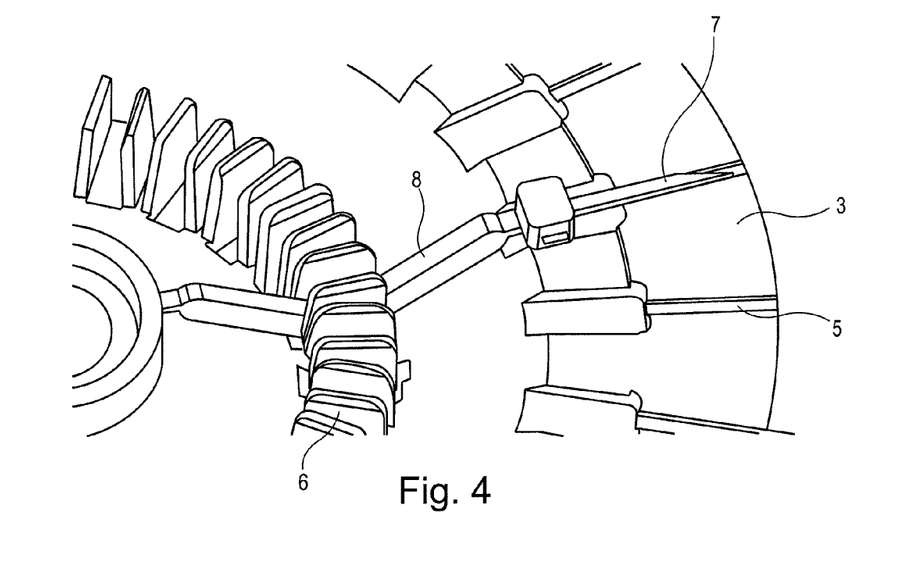
FIG. 4 is a fragmentary perspective showing a detail of FIG. 3, with the lancet arm shown in bent condition.
Figure 5:
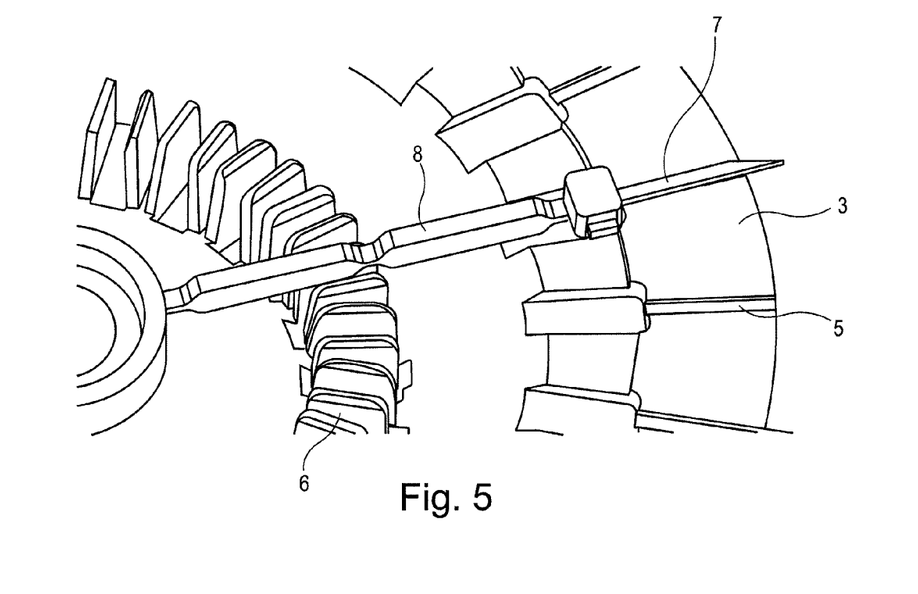
FIG. 5 is a fragmentary perspective view similar to FIG. 4, showing the lancet arm in a stretched condition.

Each of the lancets 7 is coupled with a drive mechanism in the lancet magazine 1. That drive mechanism comprises a drive arm 8 carrying the lancets 7. FIG. 4 shows the drive arm 8 in a bent starting position. During the advancing phase of a puncturing movement, the drive arm 8, being an articulated lever in the illustrated embodiment, leaves its starting position and assumes a stretched or extended position, which is illustrated in FIG. 5. As the drive arm 8 is stretched, the lancet 7 is moved in a radially outward direction so that its point exits through the exit opening 2 of the lancet magazine 1.

The drive arm 8 is coupled to a pretensioned drive element (not shown), for example, a helical spring, which is held in compressed condition between the bend of the lancet arm 8 and the housing half 3 illustrated in the Figure. When the drive mechanism is triggered, the drive element relaxes, thereby releasing mechanical energy to accelerate the lancet 7 coupled to it for a puncturing movement. Instead of a helical spring, the drive element may also consist of a tensioned rubber tape that may be fastened on the bend of the drive arm 8 and may have its other end connected with a fitted housing half.

A suitable locking mechanism retains the drive arm 8 in its starting position illustrated in FIG. 4 until a puncturing action is triggered. The locking mechanism may consist, for example, of the clamping ribs 6 that form between them a bottleneck thereby clamping the drive arm so as to hold it in the starting position illustrated in FIG. 4. The force exerted by the pretensioned drive element is chosen so that it will not suffice to force the drive arm 8 through the bottleneck. For triggering a puncturing movement, a triggering pin of the puncturing device can pass through the triggering opening 10 illustrated in FIG. 1 and may temporarily assist the pretensioned drive elements. The force supplied by the triggering pin, combined with the force of the pretensioned drive element, is sufficient to force the drive arm 8 past the bottleneck and to push the clamping ribs to the side. Once the drive arm 8 has passed the bottleneck between the clamping elements 6, it is further accelerated by the drive element to perform a puncturing movement.

The configuration of the pretensioned drive element preferably is such that once a puncturing action has been triggered, it will move the articulated lever 8 from its starting position illustrated in FIG. 4 to the position illustrated in FIG. 5 and then to an end position in which the drive arm 8 is bent in a direction opposite to the starting position. This ensures that following a puncturing action, the lancet 7 is retracted into the lancet magazine 1. Accordingly, a puncturing movement of the lancet 7 is made up by an advancing phase, in which the lancet 7 is pushed out of the lancet magazine 1, and a subsequent return phase in which the lancet 7 is retracted into the lancet magazine 1. During a return phase following the advancing phase, the drive arm 8 moves from the stretched or extended position illustrated in FIG. 5 to a bent end position where it is bent in exactly the opposite direction as in the starting position.

Figure 6:
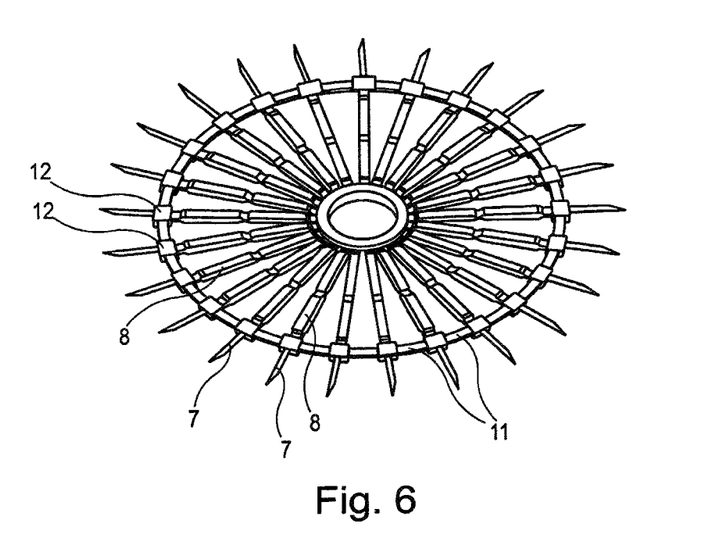
FIG. 6 illustrates in a perspective view a lancet ring for the magazine illustrated in FIG. 1, prior to isolation of the drive arms.

In principle, the lancets 7 and the drive arms 8 connected with them can be loaded into the lancet magazine 1 one by one. However, production can be made much more economical when the lancets 7 and the drive arms 8 are prefabricated as a ring which is then fitted in a housing half 3 of the lancet magazine 1 by a single operation. FIG. 6 shows one embodiment of a lancet ring with lancets 7 and drive arms 8 that can be produced at low cost by injection molding. In that case, the lancets 7 and the remaining elements of the lancet ring may be formed integrally from a hard plastic material, for example, a polycarbonate. Or the lancets 7 may be made from a different material, especially stainless steel, for being fitted in lancet holders 12 of the lancet ring.

For production of the lancets 7 and for fitting them in the lancet holders 12, it is an advantage if the lancet holders 12 are initially designed as part of a continuous ring. That ring, which connects the lancet holders 12, can be seen in FIG. 6. The lancet holders 12 are connected in this case one with the other via webs 11.

Figure 7:
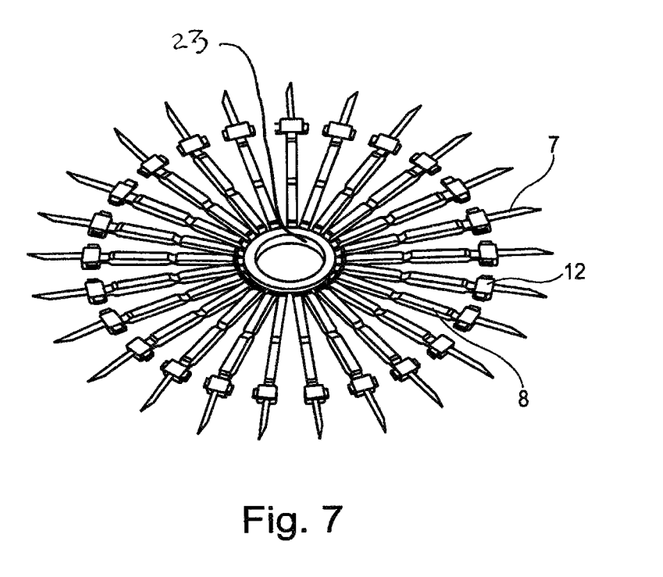
FIG. 7 illustrates in a perspective view the lancet ring illustrated in FIG. 6, after isolation of the drive arms.

Before the lancet ring is fitted in a housing half 3, the webs 11 between the lancet holders 12 are removed. This can be effected at low cost by a punching operation, for example. FIG. 7 shows a lancet ring where the webs 11 have been removed and which is ready for being fitted in a housing half 3. As can also be seen in FIG. 7, drive arms 8 extend from ring member 23.

Figure 8:
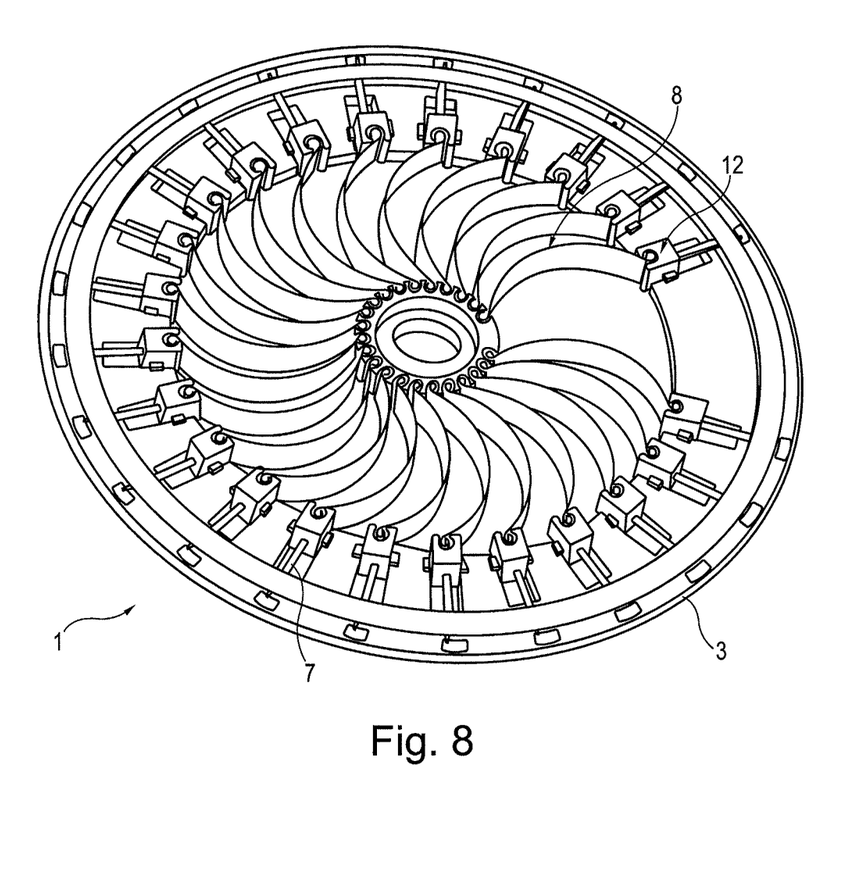
FIG. 8 is a perspective view of another embodiment of a lancet magazine showing the magazine housing in open condition.

FIG. 8 shows another embodiment of a lancet magazine 1 with the housing in open condition. The embodiment illustrated in FIG. 8 differs from the one described before especially in that the drive arms 8 are configured as leaf springs. That is, the drive arm 8 and the pretensioned drive element coupled with it of the embodiment that has been described with reference to FIGS. 1 to 7 are separate parts of the drive mechanism. By contrast, the drive arm 8 of the embodiment illustrated in FIG. 8 simultaneously is the pretensioned drive element.

Figure 9:
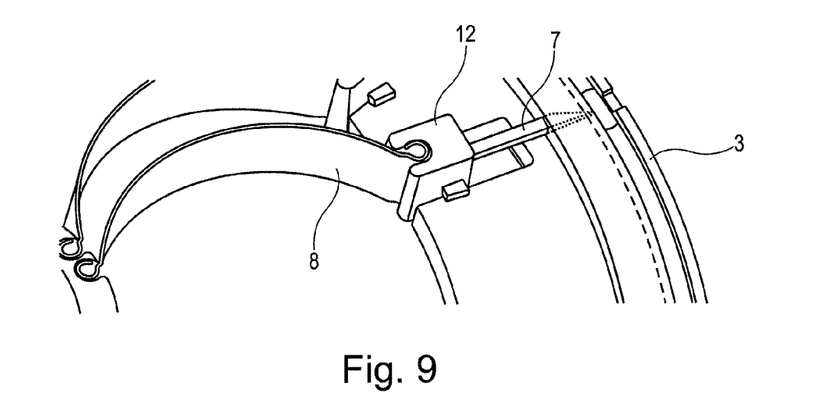
FIGS. 9-11 are fragmentary perspective views of the lancet magazine of FIG. 8 prior to, during, and following a puncturing action, respectively.
Figure 10:
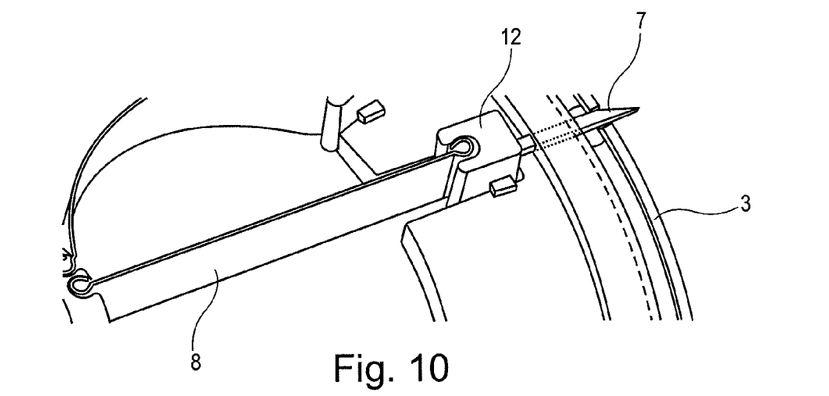
Figure 11:
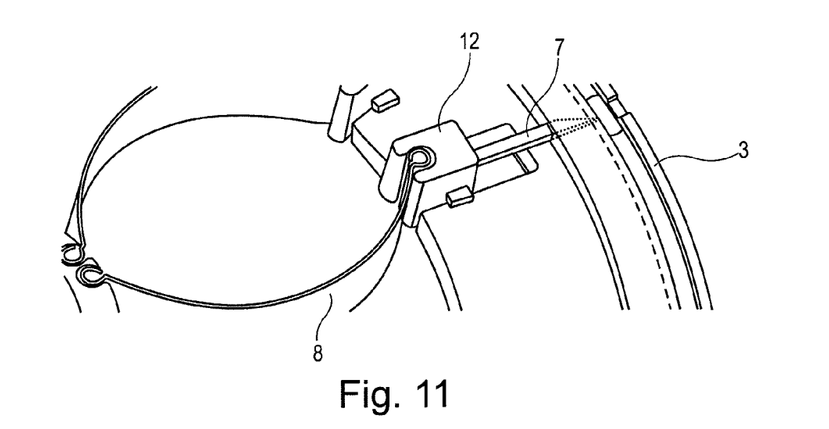

FIG. 9 shows a detail of FIG. 8, illustrating the drive arm 8 in its bent starting position. At the moment of a puncturing action, during an advancing phase of the puncturing movement, the drive arm 8 leaves that bent starting position and assumes a stretched or extended position, which is illustrated in FIG. 10. The leaf spring forming the drive arm 8 is arranged in this case to ensure that the stretched position is not a relaxed balanced position. The drive arm therefore relaxes beyond the stretched position and assumes the bent end position illustrated in FIG. 11. It is only in that end position that the drive arm 8 is untensioned. In the end position illustrated in FIG. 11, the drive arm 8 is bent in a direction opposite to the starting position illustrated in FIG. 9.

Figure 12:
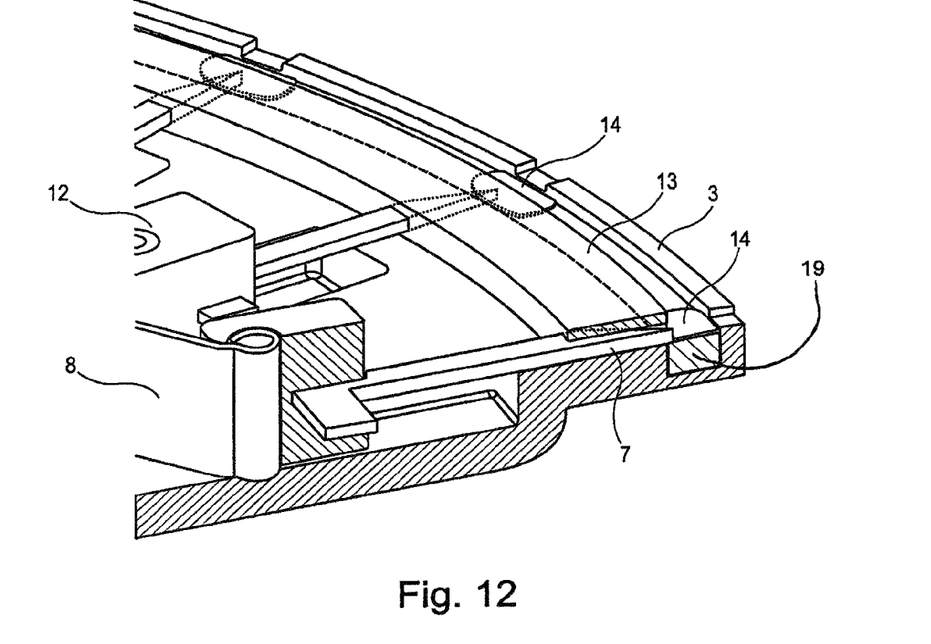
FIG. 12 is another fragmentary perspective view of the lancet magazine of FIG. 8.

The points of the lancets 7 are protected from contamination by an annular sterile protection 13 as shown in FIG. 12.

The sterile protection 13 may consist of silicone, for example, which may be applied to the lancets 7 in liquid condition after the lancets 7 have been fitted in the housing half 3 and which will then solidify. FIG. 12 shows a detail of FIG. 8 that illustrates the sterile protection 13.

The lancet magazines 1 described above may be additionally provided with test fields for examination of samples of a body liquid that have been collected by a puncturing operation. Such test fields 14 can be seen in FIG. 12. The test fields 14 preferably are provided with indicator reagents that permit an analyte concentration, for example, a glucose concentration, to be determined by photometric or electrochemical means. Corresponding test fields are used in commercially available test strips, for example, for blood-sugar determination, and therefore need not be described here in further detail.

The test fields 14 are protected by desiccants or siccatives 19 from getting impaired by humidity. The siccative 19 may be arranged, for example, in an annular groove of one housing half 3 and may be covered by test fields 14.

For photometric evaluation of a test reaction obtained using a test field 14 and a sample of a body liquid, openings are provided in the housing half that covers the test fields 14 for permitting measuring light to pass between a test field 14 and a measuring system of a puncturing device.

Figure 13:
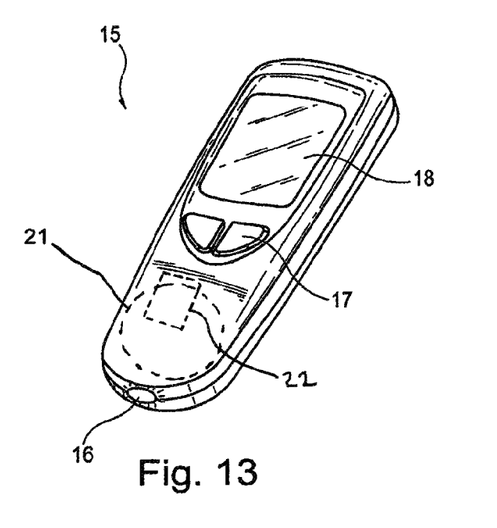
FIG. 13 is a perspective view of one embodiment of a puncturing device.

FIG. 13 shows a diagrammatic representation of one embodiment of a puncturing device 15 suited for loading the lancet magazines 1 described above. The puncturing device 15 comprises a compartment 21 shown diagrammatically in phantom in FIG. 13 for accommodation of a lancet magazine. The compartment is provided with an opening (not shown), which can be closed, e.g., on the back of the embodiment illustrated in FIG. 13.

The puncturing device 15 comprises a device opening 16 against which a part of a body is pressed for producing a puncture wound. The puncturing device further comprises operating elements 17 in the form of keys and a display 18 in the form of a liquid crystal display for displaying the examination results.

A lancet magazine 1 loaded into the puncturing device 15 is rotated by steps by a transport mechanism 22 so that the lancets contained in the lancet magazine can be used one by one for puncturing the skin of a part of a body applied to the device opening 16.

The puncturing device 15 illustrated in FIG. 13 and a lancet magazine 1 form together a puncturing system. However, a puncturing system according to the invention may also be realized as a disposable device which does not allow the lancets to be exchanged and which, consequently, is discarded after all lancets contained in it have been used. Such a disposable puncturing system comprises a plurality of lancets arranged in a housing, each being coupled with a drive mechanism that comprises, for each lancet, at least one pretensioned drive element which, when the drive mechanism is triggered, releases mechanical energy to accelerate the lancet coupled to it for a puncturing movement.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS

1 Lancet magazine
2 Exit openings
3 Housing half
4 Circumferential surfaces
5 Guide channels
6 Connection elements/clamping ribs
7 Lancets
8 Drive arm
10 Triggering openings
11 Webs
12 Lancet holders
13 Sterile protection
14 Test field
15 Puncturing device
16 Device opening
17 Operating elements
18 Display
19 Siccative
21 Compartment

What is claimed is:

1. A lancet magazine, comprising:
a plurality of lancets for generating a puncture wound for collection of a sample of a body fluid;
each lancet having a respective drive mechanism coupled thereto, each drive mechanism comprising at least one pretensioned drive element which releases mechanical energy to accelerate the respective coupled lancet for a puncturing movement when the drive mechanism is triggered; and
each drive mechanism comprising a monolithic drive arm which carries its respective lancet and which moves from a bent starting position to a stretched position during an advancing phase of a puncturing movement;
wherein each drive arm carries its respective lancet during a return phase which follows the advancing phase, each respective lancet being retracted during the return phase and each drive arm moving from the stretched position to a bent end position; and
wherein, in the bent end position, the drive arm is bent in a direction substantially opposite to the bending direction of the starting position.

2. The lancet magazine of claim 1, wherein the drive arm comprises an articulated lever.

3. The lancet magazine of claim 1, wherein the drive arm and the pretensioned drive element are separate parts of the drive mechanism.

4. The lancet magazine of claim 1, wherein the drive arm comprises the pretensioned drive element.

5. The lancet magazine of claim 1, wherein the lancets are arranged in the lancet magazine in the form of a ring.

6. The lancet magazine of claim 5, wherein the lancets extend in a radial direction.

7. The lancet magazine of claim 1, further comprising a magazine housing having a plurality of exit openings, a point of each lancet passing through a respective one of the exit openings during a puncturing movement.

8. The lancet magazine of claim 1, further comprising a puncturing device associated therewith, the puncturing device comprising:
a compartment for accommodating the lancet magazine;
a housing opening configured to be pressed against a body part in which a puncture wound is to be produced.

9. A puncturing system, comprising:
a housing in which a plurality of lancets are arranged;
each lancet having a respective drive mechanism coupled thereto, each drive mechanism comprising at least one pretensioned drive element which releases mechanical energy to accelerate the respective coupled lancet for a puncturing movement when the drive mechanism is triggered; and each drive mechanism comprising a monolithic drive arm which carries its respective lancet and which moves from a bent starting position to a stretched position during an advancing phase of a puncturing movement;

wherein each drive arm carries its respective lancet during a return phase which follows the advancing phase, each respective lancet being retracted during the return phase and each drive arm moving from the stretched position to a bent end position; and wherein, in the bent end position, the drive arm is bent in a direction substantially opposite to the bending direction of the starting position.

10. The lancet magazine of claim 1 wherein each of the plurality of drive elements are simultaneously in a pretensioned condition prior to initial use of the lancet magazine.

11. A lancet magazine, comprising:

a plurality of lancets for generating a puncture wound for collection of a sample of a body fluid;

each lancet having a respective drive mechanism coupled thereto, each drive mechanism comprising at least one pretensioned drive element which releases mechanical energy to accelerate the respective coupled lancet for a puncturing movement when the drive mechanism is triggered;

each drive mechanism comprising a drive arm which carries its respective lancet and which moves from a bent starting position to a radially extended position during an advancing phase of a puncture movement in a radial puncturing direction; and a ring member, each of the plurality of drive arms extending radially outwardly from the ring member and wherein movement of the drive arms to the radially extended position moves a respective one of the lancets in the radial puncturing direction.

12. The lancet magazine of claim 11 wherein each of the drive arms comprises a lancet holder.

13. The lancet magazine of claim 12 wherein each of the plurality of lancets are formed of steel and are fitted in one of the lancet holders.

* * * * *